(12) United States Patent
Bouzid

(10) Patent No.: US 10,527,492 B2
(45) Date of Patent: Jan. 7, 2020

(54) MODE MATCHING METHOD FOR ABSORPTION SPECTROSCOPY SYSTEMS

(71) Applicant: Li-Cor, Inc., Lincoln, NE (US)

(72) Inventor: Ahmed Bouzid, Lincoln, NE (US)

(73) Assignee: LI-COR, Inc., Lincoln, NE (US)

(*) Notice: Subject to any disclaimer, the term of this patent is extended or adjusted under 35 U.S.C. 154(b) by 0 days.

(21) Appl. No.: 15/596,695

(22) Filed: May 16, 2017

(65) Prior Publication Data

US 2018/0335344 A1   Nov. 22, 2018

(51) Int. Cl.

| | |
|---|---|
| *G01J 3/02* | (2006.01) |
| *G01J 3/10* | (2006.01) |
| *G01N 21/39* | (2006.01) |
| *G02B 17/00* | (2006.01) |
| *H01S 5/065* | (2006.01) |
| *H01S 5/00* | (2006.01) |

(52) U.S. Cl.
CPC ............ *G01J 3/0237* (2013.01); *G01J 3/021* (2013.01); *G01J 3/027* (2013.01); *G01J 3/10* (2013.01); *G01N 21/39* (2013.01); *G02B 17/004* (2013.01); *G01N 2201/0636* (2013.01); *G01N 2201/06113* (2013.01); *H01S 5/0071* (2013.01); *H01S 5/0656* (2013.01)

(58) Field of Classification Search
CPC .. G01J 3/0237; G01J 3/027; G01J 3/10; G01J 3/021; H01S 3/0071; G02B 17/004; G01N 21/39; G01N 2201/0636; G01N 2201/06113

See application file for complete search history.

(56) References Cited

U.S. PATENT DOCUMENTS

| | | | |
|---|---|---|---|
| 4,793,709 A | 12/1988 | Jabr et al. | |
| 5,134,622 A | * 7/1992 | Deacon | G02F 1/39 |
| | | | 307/424 |
| 5,432,610 A | 7/1995 | King et al. | |
| 5,528,040 A | 6/1996 | Lehmann | |

(Continued)

OTHER PUBLICATIONS https://en.wikipedia.org/wiki/Gaussian_beam.*

(Continued)

*Primary Examiner* — Mohamed K Amara
(74) *Attorney, Agent, or Firm* — Leydig, Voit & Mayer, Ltd.; Gerald T. Gray

(57) ABSTRACT

Systems and methods for controlling optical feedback in an optical system having a radiation source optically coupled via mode matching optics with a resonant optical cavity. The cavity includes at least two cavity mirrors, one of which is a cavity coupling mirror, and has a plurality of optical resonance cavity modes, wherein the radiation source emits a beam of continuous wave radiation and is capable of being scanned whereby a mean optical frequency of the continuous wave radiation beam is adjustable over a range of frequencies, wherein the radiation source is responsive to optical feedback radiation emerging from the cavity, and wherein the mode matching optics couples the beam of continuous wave radiation to the cavity via the cavity coupling mirror. The radiation source and the mode matching optics are aligned so that a mode fill ratio is reduced relative to a maximum mode fill ratio, wherein for the maximum mode-fill ratio the laser beam is coupled with a fundamental cavity mode.

28 Claims, 7 Drawing Sheets

(56) References Cited

U.S. PATENT DOCUMENTS

| | | | |
|---|---|---|---|
| 5,684,623 A * | 11/1997 | King | H01S 3/082 359/346 |
| 5,723,864 A * | 3/1998 | Atkinson | G01N 21/3504 250/339.13 |
| 5,903,358 A * | 5/1999 | Zare | G01J 3/10 250/343 |
| 5,912,740 A * | 6/1999 | Zare | G01J 3/10 356/437 |
| 5,917,188 A * | 6/1999 | Atkinson | G01N 21/3504 250/339.13 |
| 5,999,547 A * | 12/1999 | Schneider | G02F 1/39 359/330 |
| 6,038,055 A * | 3/2000 | Hansch | H01S 3/082 359/264 |
| 6,084,682 A * | 7/2000 | Zare | G01N 21/39 356/437 |
| 6,094,267 A * | 7/2000 | Levenson | G01J 3/30 356/484 |
| 6,222,860 B1 * | 4/2001 | Pittaro | G01N 21/39 372/19 |
| 6,233,052 B1 * | 5/2001 | Zare | G01N 21/39 250/343 |
| 6,504,145 B1 | 1/2003 | Romanini et al. | |
| 6,611,546 B1 * | 8/2003 | Garnache | H01S 5/02288 372/92 |
| 6,845,108 B1 * | 1/2005 | Liu | H01S 3/1109 372/20 |
| 7,012,696 B2 * | 3/2006 | Orr | G01J 3/42 356/437 |
| 7,450,240 B2 | 11/2008 | Morville et al. | |
| 7,535,573 B2 | 5/2009 | Kachanov et al. | |
| 7,569,823 B2 * | 8/2009 | Miller | G01N 21/39 250/339.07 |
| 7,606,274 B2 * | 10/2009 | Mirov | C30B 31/00 372/10 |
| 7,678,003 B2 | 3/2010 | Janson et al. | |
| 8,154,727 B2 * | 4/2012 | Dreyer | G01J 3/02 356/432 |
| 8,327,686 B2 * | 12/2012 | Kachanov | G01N 21/1702 73/24.02 |
| 8,437,000 B2 * | 5/2013 | Cole | G01N 21/031 356/436 |
| 8,659,758 B2 | 2/2014 | Koulikov et al. | |
| 8,659,759 B2 | 2/2014 | Koulikov et al. | |
| 8,665,442 B2 | 3/2014 | Koulikov et al. | |
| 8,976,834 B2 * | 3/2015 | Kaster | H01S 3/0057 372/92 |
| 8,982,352 B1 * | 3/2015 | Hoffnagle | H01S 5/0687 250/573 |
| 8,992,836 B2 * | 3/2015 | Nitkowski | G01N 21/7746 385/12 |
| 9,012,851 B2 * | 4/2015 | Scherer | G01N 21/3504 250/353 |
| 9,194,742 B2 | 11/2015 | Kachanov et al. | |
| 9,304,080 B2 | 4/2016 | Kachanov et al. | |
| 9,581,492 B2 | 2/2017 | Koulikov | |
| 9,651,488 B2 * | 5/2017 | Scherer | G01N 21/61 |
| 9,759,654 B2 | 9/2017 | Koulikov et al. | |
| 9,778,110 B1 * | 10/2017 | Rella | G01J 3/42 |
| 2005/0134836 A1 * | 6/2005 | Paldus | G01J 3/44 356/73 |
| 2005/0254534 A1 * | 11/2005 | Loewen | G02B 5/10 372/32 |
| 2006/0232779 A1 * | 10/2006 | Shaw | G01J 3/42 356/436 |
| 2006/0268949 A1 * | 11/2006 | Gohle | G02F 1/353 372/21 |
| 2007/0195319 A1 * | 8/2007 | Kachanov | G01J 3/42 356/300 |
| 2007/0195434 A1 * | 8/2007 | Koulikov | G01N 21/39 359/809 |
| 2008/0111077 A1 * | 5/2008 | Miller | G01N 21/39 250/339.07 |
| 2008/0259969 A1 * | 10/2008 | Piper | H01S 3/1086 372/3 |
| 2011/0073784 A1 * | 3/2011 | Kartner | H05G 2/00 250/504 R |
| 2015/0276590 A1 * | 10/2015 | Koulikov | G01N 21/1702 356/72 |
| 2016/0011101 A1 * | 1/2016 | Ognibene | G01N 21/3103 356/437 |

OTHER PUBLICATIONS

Written Opinion, dated May 3, 2018, in International Patent Application No. PCT/US18/25331.

Anderson, Dana Z., "Alignment of Resonant Optical Cavities" *Applied Optics* vol. 23, No. 17, Sep. 1, 1984.

* cited by examiner

MODE MATCHING METHOD FOR ABSORPTION SPECTROSCOPY SYSTEMS

FEDERALLY SPONSORED RESEARCH OR DEVELOPMENT

This invention was made with Government support under Grant Number DE-AR0000537, awarded by the U.S. Department of Energy, Advanced Research Projects Agency-Energy (ARPA-E). The Government has certain rights in this invention.

BACKGROUND

The present invention relates generally to trace gas detection and more specifically to cavity-based spectroscopy systems and methods for measuring one or more trace gases.

In cavity enhanced optical absorption spectroscopy systems and methods, radiation of a laser is directed into a resonant optical cavity, and the optical intensity inside the cavity is observed. The optical frequency of the laser can be periodically scanned. If it is assumed for clarity that the laser linewidth is much smaller than the cavity resonance width, at the moment when the laser light frequency coincides with a cavity mode transmission peak the optical intensity inside the resonant optical cavity reflects total cavity loss, and the total cavity loss can be quantitatively determined provided that the incident intensity and cavity parameters are known. The total cavity loss is a sum of the cavity mirror losses and losses caused by absorption of a gas mixture present in the cavity. The lower the cavity mirror losses, or equivalently, the higher each mirror's reflectivity—the smaller the absorption of the intra-cavity gas mixture that can be detected. With very high reflectivity mirrors, the laser linewidth will become too large compared to the cavity resonance width, thus limiting achievable enhancement of the gas mixture absorption by the cavity. This can be helped by narrowing the laser linewidth using optical feedback from the cavity and a laser that is sensitive or responsive to optical feedback from the cavity. With such a feedback sensitive laser, during the scan, as the frequency of the laser light approaches the frequency of one of the cavity modes, the laser locks to that mode, i.e., the laser linewidth becomes much smaller than the resonance mode width, and that regardless whether the frequency scan range of the unlocked laser may be large, in a locked condition the optical frequency of the laser will change only within the resonance peak. As the laser frequency scan continues, the laser will lose the lock to the current cavity mode and relock to the next cavity mode that it approaches. Due to the optical feedback effect, the laser optical frequency during the scan will essentially take the number of discrete values corresponding to the peaks of the cavity mode resonances that are equidistant in optical frequency. A discrete absorption spectrum of the analyzed gas can thus be obtained by sequential coupling to the entire set of the cavity modes within the scan range, and the trace gas concentration can be derived from the absorption spectrum. This sub-family of cavity-based spectroscopy systems and methods that uses optical feedback will be referred to as optical feedback cavity enhanced absorption spectroscopy (OF CEAS).

In OF CEAS, the strength of the optical feedback from the resonance cavity to the laser should be within certain limits, otherwise it may not be possible to provide reproducible scan-to-scan mode coupling as the laser scans. Previous OF CEAS systems strive to optimize optical power coupled into an external optical cavity in a manner that enhances cavity feedback. Such coupling requires weak optical feedback to the laser such that the resonant enhancement does not last more than one Free-Spectral-Range (FSR). In known OF CEAS systems and methods, complex optical components are used to control the feedback. Such components include Faraday isolators, variable optical attenuators, or polarization rotators. One example is provided in U.S. Pat. No. 7,450,240, which uses a settable attenuator element such as a Faraday Isolator to control the amount of light fed back towards the laser. The settable attenuator actively reduces the feedback light emerging from the cavity, and incident upon the laser, to a desirable level. This does provide a way to control the feedback but at the expense of added complexity, cost, and added sources of noise and instability. For example, adverse interference effects, temperature drifts and aging drifts may result from these components in the system. Achieving high stability and high reproducibility of the optical absorption measurements becomes a major problem in such systems.

U.S. Pat. No. 8,659,758 avoids the complications in the system design of U.S. Pat. No. 7,450,240 by specifying that one of the mirrors of the external cavity (the coupling mirror) have a low transmission level. This is a much simpler approach compared to U.S. Pat. No. 7,450,240 and avoids the disadvantages associated therein. However, the approach in U.S. Pat. No. 8,659,758 presents challenges of its own. For example, the low transmission requirement is difficult to achieve batch-to-batch, and when other components of the design change, such as the laser, the amount of transmission of the coupling mirror needs to be changed accordingly. These challenges may present difficulties in a production environment.

SUMMARY

The present disclosure generally provides systems and methods for coupling light into an external optical cavity, and more particularly to systems and methods for adjusting the mode fill-ratio to achieve controllable optical feedback.

Embodiments of the present invention provide methods and systems for controlling or adjusting the coupling conditions of laser light or other radiation coupled into an external cavity such that the fill-ratio of optical feedback modes is in a desired range. The present embodiments advantageously enable adjusting or controlling the mode-matching conditions to achieve a mode fill-ratio that provides optimum or desired optical feedback to an optical feedback sensitive radiation source, rather than achieving maximum optical power.

According to an embodiment, a method is provided for controlling optical feedback in an optical system having a radiation source optically coupled via mode matching optics with a resonant optical cavity having at least two cavity mirrors, one of which is a cavity coupling mirror, the cavity having a plurality of optical resonance cavity modes, wherein the radiation source emits a beam of continuous wave radiation and is capable of being scanned whereby a mean optical frequency of the continuous wave radiation beam is adjustable over a range of frequencies, wherein the radiation source is responsive to optical feedback radiation emerging from the cavity, and wherein the mode matching optics couples the beam of continuous wave radiation to the cavity via the cavity coupling mirror. The method typically includes aligning the radiation source and the mode matching optics so that a mode fill ratio is reduced relative to a maximum mode fill ratio, wherein for the maximum mode-fill ratio the laser beam is coupled with a fundamental cavity mode. For example, in certain aspects, the aligning the radiation source and the mode matching optics includes aligning or setting a relative distance between the radiation source and a component of the mode matching optics to achieve the maximum mode fill ratio, and thereafter adjusting the relative distance between the radiation source and the component of the mode matching optics to attain the reduced mode fill ratio.

In certain aspects, the adjusting includes reducing the relative distance between the radiation source and the component of the mode matching optics, so that a beam waist size of the continuous wave radiation beam is diverging at the cavity coupling mirror. In certain aspects, the adjusting includes increasing the relative distance between the radiation source and the component of the mode matching optics, so that a beam waist of the continuous wave radiation beam is converging at the cavity coupling mirror. In certain aspects, the adjusting includes moving only the radiation source. In certain aspects, the adjusting includes moving only the component of the mode matching optics or multiple components of the mode matching optics. In certain aspects, the adjusting includes moving both the radiation source and the component of the mode matching optics, or the radiation source and the multiple components of the mode matching optics. In certain aspects, the adjusting includes reducing the relative distance between the radiation source and the component of the mode matching optics, so that a beam waist size of the continuous wave radiation beam is smaller or larger than a beam waist size of the radiation circulating in the cavity. In certain aspects, the cavity has a configuration selected from the group consisting of a ring cavity having three or more cavity mirrors, a linear cavity having two or more cavity mirrors, and a V-shaped cavity having three cavity mirrors.

According to another embodiment, an optical system is provided that typically includes a resonant optical cavity having at least two cavity mirrors, one of which is a cavity coupling mirror, the cavity having a plurality of optical resonance cavity modes, and a radiation source that emits a beam of continuous wave radiation, wherein the radiation source is capable of being scanned whereby a mean optical frequency of the continuous wave radiation is adjustable over a range of frequencies, and wherein the radiation source is responsive to optical feedback radiation emerging from the cavity. The optical system also typically includes mode matching optics configured to couple the beam of continuous wave radiation to the cavity via the cavity coupling mirror, the mode matching optics including at least one component, and an adjustment mechanism coupled with one or both of the at least one component of the mode matching optics and the radiation source, the adjustment mechanism configured to adjust a relative position of the radiation source relative to the at least one component of the mode matching optics such that a mode fill ratio of the continuous wave radiation beam with respect to the cavity is reduced relative to a maximum mode fill ratio of the beam with respect to the cavity.

In certain aspects, the adjustment mechanism includes an actuator configured to adjust the relative position of the radiation source and the at least one component of the mode matching optics in response to a control signal. In certain aspects, the control signal is provided by a control system in response to receiving a user input to adjust the relative position of the radiation source and the at least one component of the mode matching optics. In certain aspects, the system further includes a detector configured to measure an intensity of an intra-cavity optical power of radiation circulating in the cavity, wherein the control signal is provided by a control system in response to receiving a feedback signal from the detector. In certain aspects, the cavity has a configuration selected from the group consisting of a ring cavity having three or more cavity mirrors, a linear cavity having two or more cavity mirrors, and a V-shaped cavity having three cavity mirrors. In certain aspects, the system further includes a means for adjusting the mean optical frequency of the radiation source so as to scan the mean optical frequency of the radiation source over a cavity resonance peak. In certain aspects, the cavity is capable of being scanned whereby an optical frequency of a cavity resonance mode peak is adjustable over a range of frequencies. In certain aspects, the system further includes a means for controlling a position of one of the cavity mirrors so as to scan the optical frequency of the cavity resonance mode peak. In certain aspects, the system further includes a detector configured to measure an intensity of the intracavity optical power of radiation circulating in the cavity and to generate a signal representing the intracavity optical power of radiation circulating in the cavity, wherein the cavity includes a gaseous medium including one or more analyte species.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE SEVERAL VIEWS OF THE DRAWING(S)

The detailed description is described with reference to the accompanying figures. The use of the same reference numbers in different instances in the description and the figures may indicate similar or identical items.

DETAILED DESCRIPTION

Figure 1:
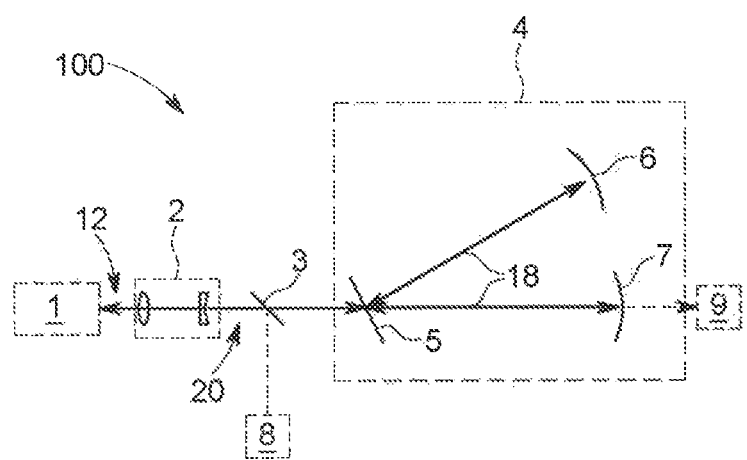
FIG. 1 illustrates a cavity enhanced absorption spectroscopy (CEAS) system according to one embodiment.

FIG. 1 illustrates a cavity enhanced absorption spectroscopy (CEAS) system 100 according to one embodiment. As shown, CEAS system 100 includes a radiation source 1 that emits continuous wave coherent radiation, such as continuous wave laser light, an optical cavity 4 and two detectors, detector 8 and detector 9. As shown, cavity 4 is a V-shaped cavity defined by cavity coupling mirror 5 and end mirrors 6 and 7. It should be appreciated that the cavity could be a linear cavity with two or more mirrors, or a ring shaped cavity with three or more mirrors, or may have any other structure having three or more mirrors. An enclosure or housing (not shown) provides an air tight seal for cavity 4 such as to allow control of the environment within the housing and hence the cavity 4. The enclosure may also house other components of system 100 such as the radiation source 1 and components between radiation source 1 and cavity 4. One or more optical components 2 (collectively referred to as mode matching optics 2) are configured and arranged to facilitate directing radiation from source 1 to the optical cavity 4 via cavity coupling mirror 5 and to ensure the mode matching of the radiation source (e.g., laser) to the cavity. As used herein below, radiation source 1 may be referred to as laser 1 or laser source 1 or light source 1, and that radiation may also be referred to as "light", however, it should be understood that a laser is merely an example of a useful radiation source and that the radiation source may include any radiation source that is capable of emitting a beam of radiation having a desired wavelength or controllable to emit a beam of radiation over a range of desired wavelengths. Useful wavelengths include wavelengths in the visible spectrum, in the infrared spectrum, the ultraviolet spectrum and any other spectrum as may be desired.

In the embodiment shown in FIG. 1, a beam splitting element 3 is positioned and aligned so as to allow substantially all of the incident light 12 emitted or generated by light source 1 to impinge on cavity coupling mirror 5. A small portion of the incident light beam 12 is directed (e.g., reflected or refracted) by element 3 to detector 8. Cavity coupling mirror 5, in this embodiment, is arranged at an angle with respect to beam 12, although it could be perpendicular to beam 12. A portion of incident light 12 enters cavity 4 via mirror 5 as intra-cavity light 18. The remainder of light 12 is reflected away by mirror 5. Depending on the frequency of incident light 12 and the optical length of cavity 4 (e.g., optical length from mirror 7 to mirror 5 to mirror 6) light 18 circulating in the cavity may build up and resonate at one or a plurality of cavity modes defined by the optical length of the cavity. A portion of the intra-cavity light 18 circulating in cavity 4 between mirrors 7, 5 and 6, emerges or escapes via mirror 5 and impinges on element 3. Element 3 allows a portion 20 to pass back to light source 1.

In certain aspects, radiation source 1 includes a laser or other coherent light source that is sensitive or responsive to optical feedback. One useful laser is a semiconductor diode laser that is sensitive to optical feedback from light 20 impinging on the laser from the cavity, e.g., from coupling mirror 5 in the current configuration. In general, useful laser sources might include diode lasers, quantum cascade lasers and solid state lasers, any external cavity laser, etc.

Light source 1 is also preferably capable of being frequency scanned, whereby a mean optical frequency of the emitted radiation beam (e.g., laser beam) is adjustable over a range of frequencies. This can be accomplished as is well known, such as, for example, by adjusting the current applied to a diode laser and/or adjusting a temperature of a laser medium. In certain aspects, the cavity 4 is also capable of being frequency scanned, e.g., by changing or adjusting an optical length of the cavity, whereby an optical frequency of a cavity resonance peak is adjustable over a range of frequencies. Adjustment of the optical length of the cavity can include adjusting or modulating a relative position of one or more of the cavity mirrors, adjusting a pressure of the medium within cavity 4 or other ways as are known to one skilled in the art.

Figure 2:
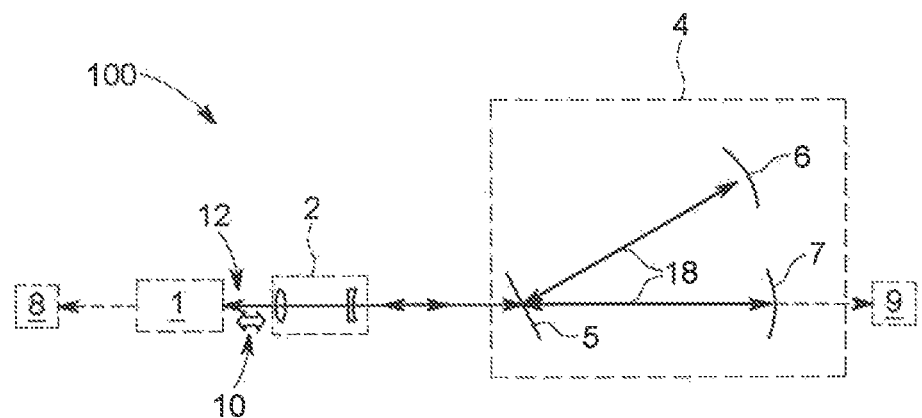
FIG. 2 shows an alternate configuration for a CEAS system according to an embodiment.
Figure 3:
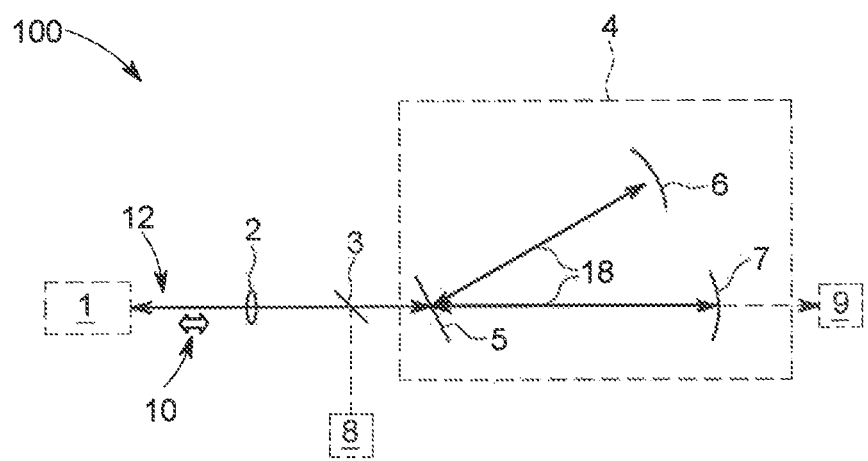
FIG. 3 shows another alternate configuration for a CEAS system according to an embodiment.

FIG. 2 and FIG. 3 each show alternative configurations of CEAS system 100 similar to the system shown in FIG. 1. In FIG. 2, the detector 8 is positioned "behind" the radiation source 1 and is configured to detect light exiting the backside of source 1. In FIG. 3, the mode matching optics 2 is shown as including a single component, such as a lens element. However, it should be appreciated that the mode matching optics 2 may include a single component or element, e.g., lens or other optical element, or it may include multiple optical components or elements working in concert to direct the radiation beam to the cavity coupling mirror and to condition the mode matching characteristics (e.g., waist size, axis, convergence or divergence of the beam) of the radiation beam at the cavity coupling mirror so as to align the beam and cavity as desired.

In certain embodiments, CEAS system 100 is useful for detecting one or more trace gases within a gas mixture present in the cavity 4. When the frequency of the light 12 emitted by source 1 approaches the frequency of one of the cavity modes, the light 12 entering the cavity 4 as light 18 begins to fill the cavity in that mode. The optical intensity of the light 18 circulating inside the resonance cavity reflects total cavity loss at the moment when the light frequency of light 12 coincides with the cavity mode transmission peak. The total cavity loss is a sum of the cavity mirror losses and losses caused by absorption by one or more components of a gas mixture present in the cavity 4. Analyte absorption, e.g., absorption losses caused by absorption by the one or more gas components, is determined based on the difference of the cavity loss when the absorbing component is present, such as in an analyzed gas, and the cavity loss when the absorbing component is absent, such as in a reference gas. Absorption measurements can be made by way of direct absorption measurements or cavity ring-down measurements as are well known to those skilled in the art.

In the embodiment shown in FIG. 1, the mode-fill ratio (or mode-filling ratio) of cavity modes is typically set to an initial alignment condition that result in a maximum mode fill ratio. For a proper, optimal initial alignment of a laser beam to a cavity, the laser beam should couple to the fundamental spatial mode(s) of the cavity and should not couple to higher-order spatial modes of the cavity. An unmatched waist size between the laser beam and the cavity and/or a transverse displacement or angular displacement of the laser beam waist relative to the cavity axis and waist size may result in coupling of the beam to higher order transverse modes of the cavity, which is generally undesirable and results a reduced mode-fill ratio. As used, herein, a maximum mode-fill ratio (or mode-filling ratio) refers to the alignment conditions where the input laser beam couples to a fundamental spatial mode or modes of a cavity but not to higher order modes, and provides a maximum signal or power coupling. For example, for a Gaussian input beam, an optimum mode fill ratio may be achieved by aligning the beam axis with the cavity axis and by matching the spatial laser beam waist size with the cavity beam waist size. As used herein, a reduced mode-fill ratio (or mode-filling ratio) refers to the alignment conditions where the input laser beam couples to the fundamental spatial mode or modes of a cavity, but does not provide a maximum signal or power coupling to the cavity, and may also couple to one or more higher order modes. For example, for a Gaussian input beam, a reduced mode-fill ratio may be achieved by aligning the beam axis with the cavity axis and by reducing or increasing the spatial laser beam waist size relative to the cavity beam waist size at the cavity coupling mirror.

In certain embodiments, the alignment of the input laser beam and the cavity is altered or adjusted so that a reduced mode-fill ratio is achieved. This may be done, for example, by altering the input beam waist size at the cavity coupling mirror (which creates a beam waist size mismatch), and/or by misaligning or tilting the axis of the input beam and the axis of the cavity slightly, and/or by creating a divergent or convergent beam (typically also with a beam waist size mismatch) at the cavity coupling mirror. Adjusting the system parameters to achieve a reduced mode fill ratio advantageously enables control of the optical feedback radiation (i.e., intensity) fed back to the feedback sensitive light source 1 (e.g., diode laser or other optical feedback sensitive laser or radiation source).

Figure 4:
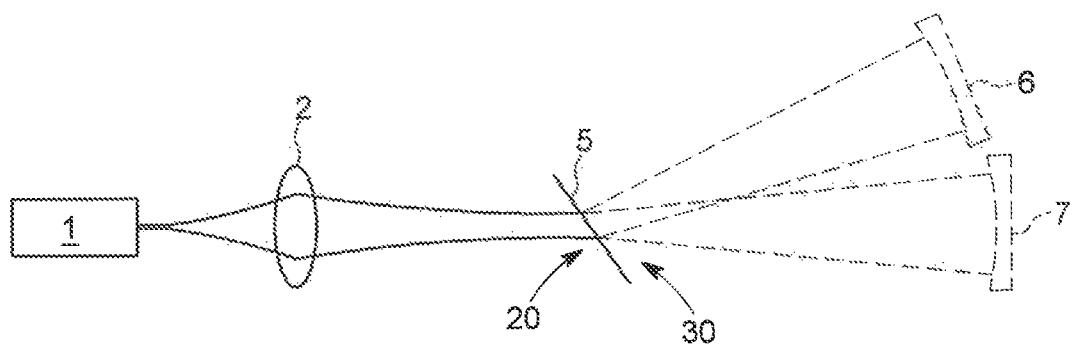
FIG. 4 shows an example of initial laser-to-cavity alignment or coupling conditions wherein the input beam waste size matches the cavity beam waste size so as to provide optimum power and maximum spectral mode filling.

In an embodiment as shown in FIG. 2, the mode-matching optics 2 is designed so that, for an initial alignment condition, the mode size coming from the light source 1 matches the waist size and location of the cavity mode to provide optimum power and maximum spectral mode filling. FIG. 4 shows an example of initial laser-to-cavity alignment or coupling conditions wherein the input beam waste size matches the cavity beam waste size so as to provide optimum power and maximum spectral mode filling.

In an embodiment, the spacing or distance between the light source 1 and mode-matching optics 2 is adjusted to change the mode filling-ratio of the signal output by the external cavity 4 and detected by detector 9. In certain embodiments, the distance is set after manual adjustment by a user. In another embodiment, an adjustment mechanism 10 is provided to automatically and controllably adjust the distance between the radiation source 1 and the mode matching optics 2 in response to a control signal. For example, in an embodiment, a relative distance between the radiation source and a component of the mode matching optics is initially aligned or set to achieve the maximum mode fill ratio, and thereafter the relative distance between the radiation source and the component of the mode matching optics is adjusted to attain the desired reduced mode fill ratio.

The adjustment mechanism 10 may include a mechanical actuator configured to adjust a position of the connected element or elements, such as by linearly moving the connected element(s) in a particular direction in response to a control signal. In the examples shown in FIG. 2 and FIG. 3, for example, an actuator or other mechanical element may be coupled to the radiation source 1 and configured to move the radiation source 1 away from or towards the mode matching optics, or an actuator or other element may be coupled to one or more components of the mode matching optics and configured to move the connected mode matching component(s) in a linear manner (e.g., toward or away from the radiation source 1), such that the desired beam waste size at the cavity coupling mirror is achieved. In certain embodiments, separate actuators may be coupled with each of the radiation source 1 and the one or more components of the mode matching optics to control relative positions of the connected element(s).

Figure 5:
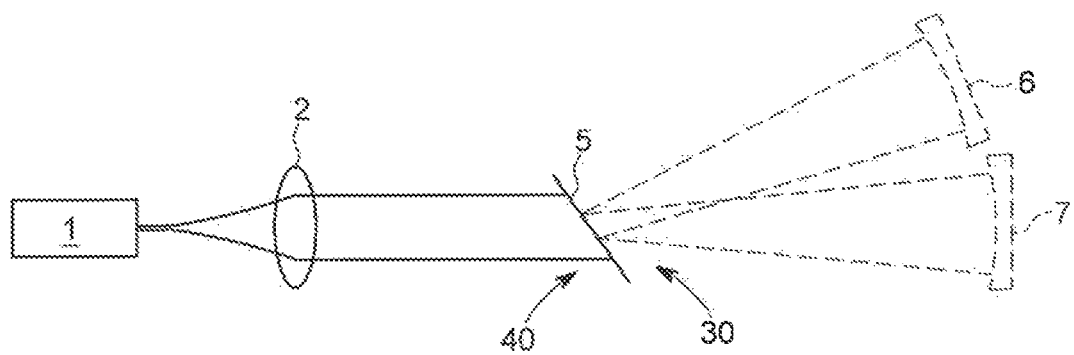
FIG. 5 and FIG. 6 show two examples of the effect of adjusting the laser-mode matching optics distance on the laser mode size and location relative to the cavity mode size and location.
Figure 6:
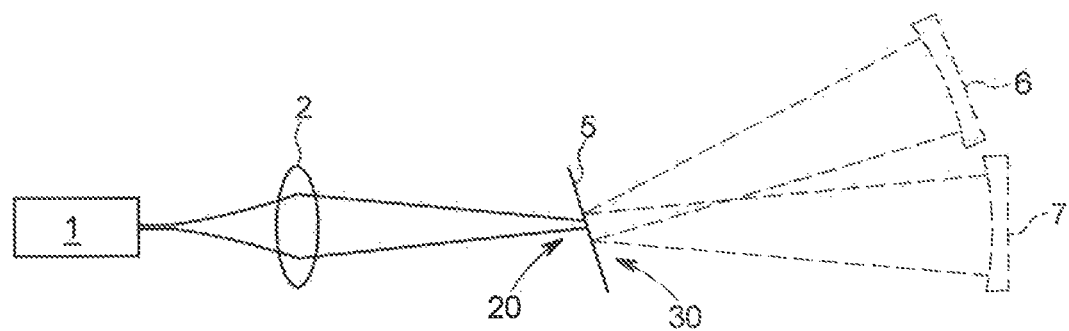

FIG. 5 and FIG. 6 show two examples of the effect of adjusting the laser-mode matching optics distance on the laser mode size and location relative to the cavity mode size and location. For example, as shown in FIG. 5, the distance between the radiation source 1 and the mode matching optics 2 is decreased to produce a divergent beam of radiation interacting with the cavity mirror 5. Decreasing the distance may be accomplished, as an example, by moving one or both of the radiation source 1 and/or a component of the mode matching optics 2 towards the other. Under these conditions, with a diverging radiation beam 40 (and increased beam waist size), the mode filling ratio is reduced relative to the initial, maximum mode-filling ratio. As shown in FIG. 6, the distance between the radiation source 1 and the mode matching optics 2 is increased to produce a converging beam of radiation interacting with the cavity mirror 5. Increasing the distance may be accomplished, as an example, by moving one or both of the radiation source 1 and/or a component of the mode matching optics 2 away from the other. Under these conditions, with a converging radiation beam 20 (and decreased beam waist size), the mode filling ratio is reduced relative to the initial, maximum mode-filling ratio.

Figure 7:
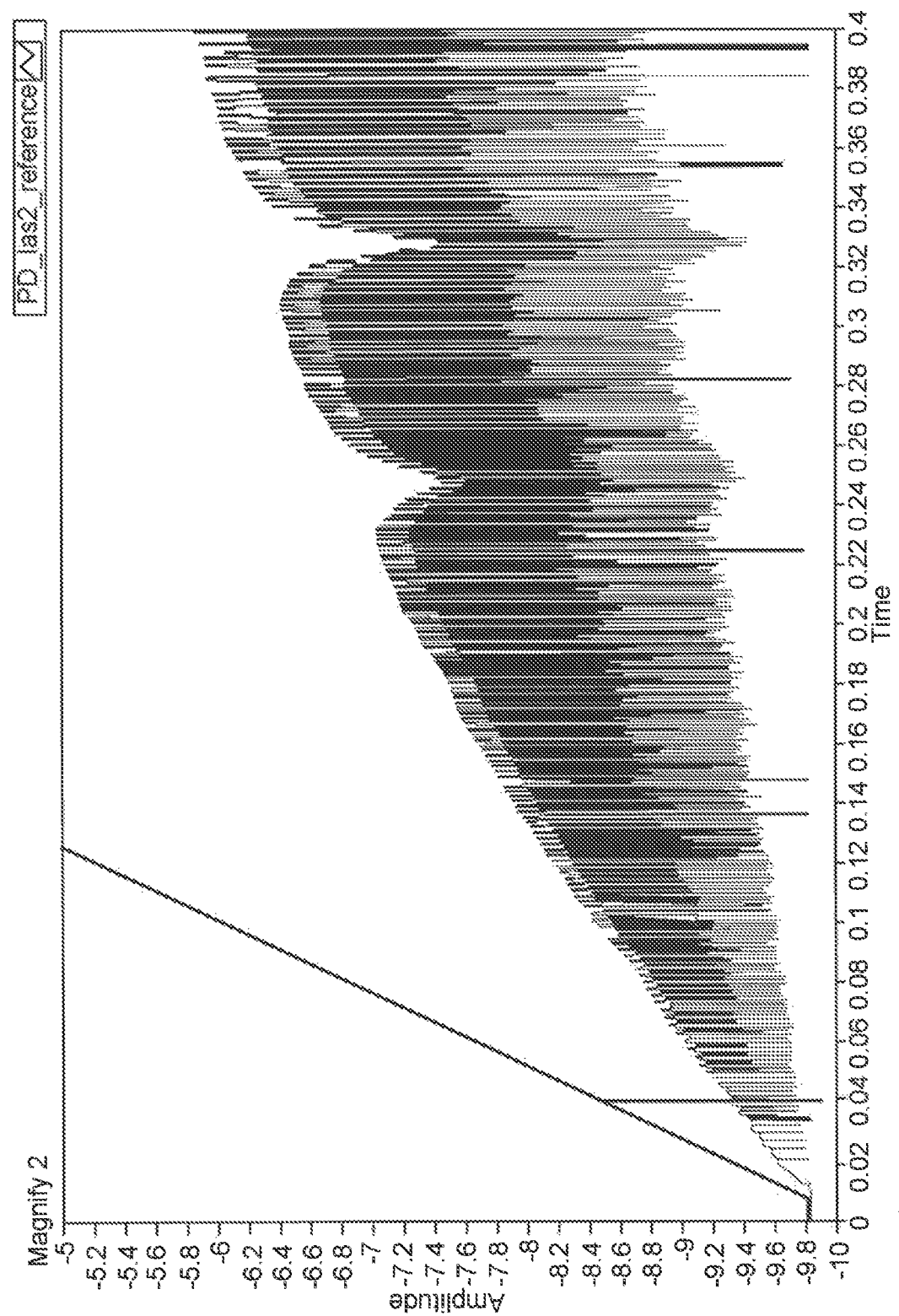
FIG. 7 and FIG. 8 show an example of mode structure measurements for an embodiment of a system with a distance between the radiation source and mode matching optics adjusted from an in initial alignment condition (e.g., maximum mode-fill ratio) to a condition that results in a high fill-ratio.
Figure 8:
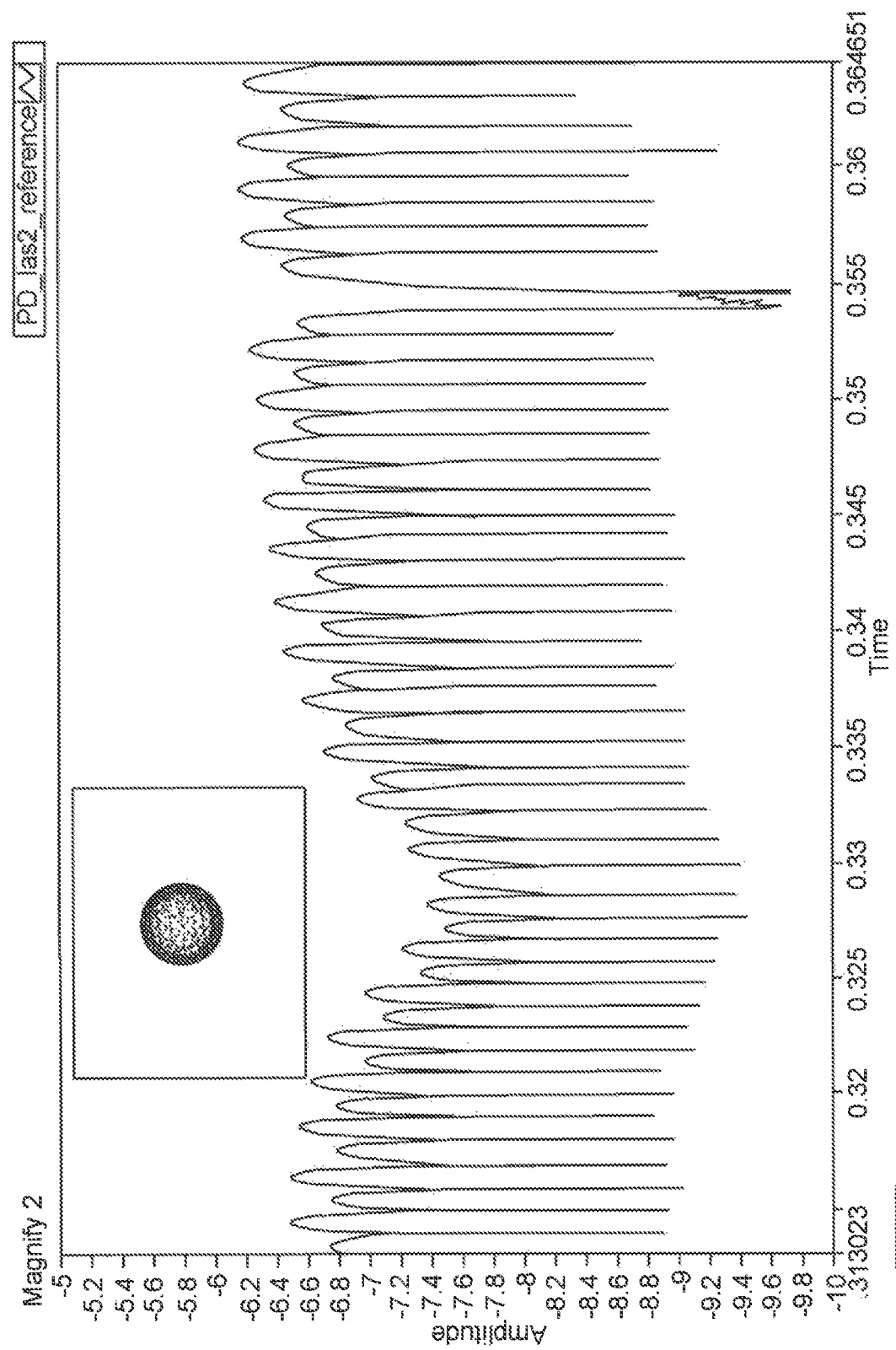
Figure 9:
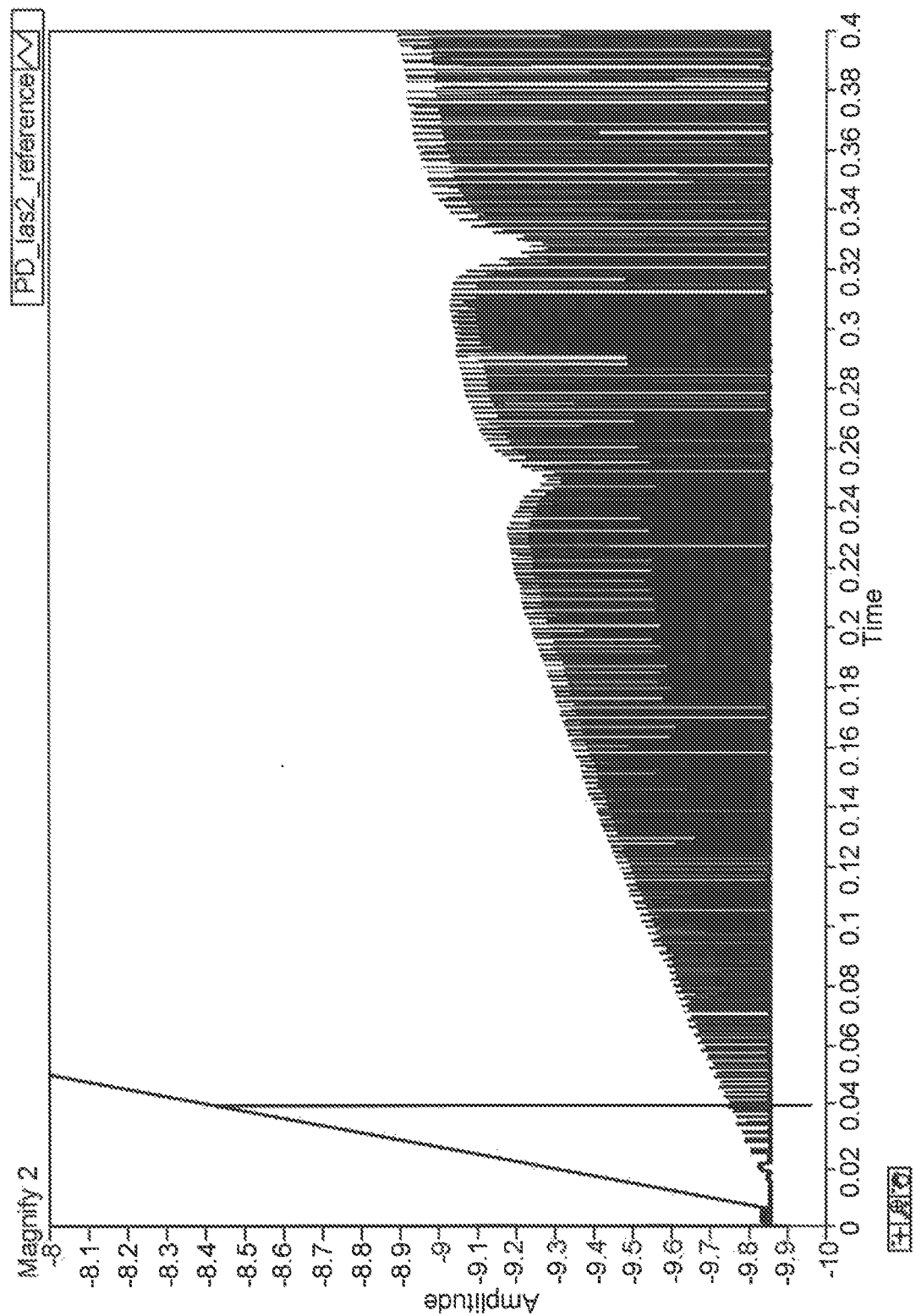
FIG. 9 and FIG. 10 show measurements from the same system used for the measurements of FIG. 7 and FIG. 8, but with a distance between the radiation source and mode matching optics adjusted to result in a lower fill-ratio.
Figure 10:
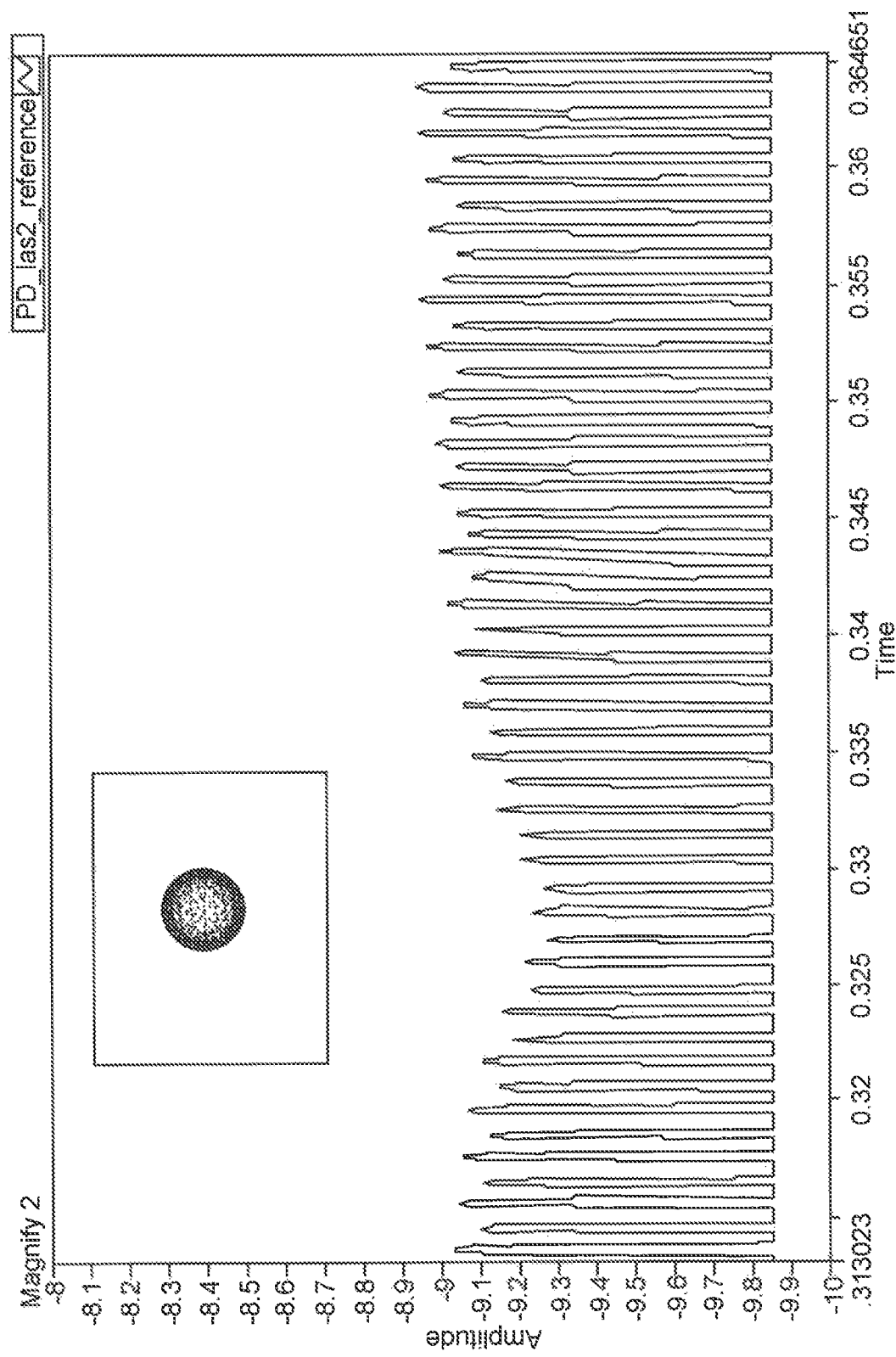

FIG. 7 and FIG. 8 show an example of mode structure measurements for an embodiment of a system with a distance between the radiation source and mode matching optics adjusted from an in initial alignment condition (e.g., maximum mode-fill ratio) to a condition that results in a high fill-ratio. FIG. 9 and FIG. 10 show measurements from the same system used for the measurements of FIG. 7 and FIG. 8, but with a distance between the radiation source and mode matching optics adjusted to result in a lower fill-ratio. The latter case may be more desirable because, in this particular example, it does not result in skipped modes and therefore provides a better performance.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the disclosed subject matter (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or example language (e.g., "such as") provided herein, is intended merely to better illuminate the disclosed subject matter and does not pose a limitation on the scope of the invention unless otherwise claimed. No language in the specification should be construed as indicating any non-claimed element as essential to the practice of the invention.

Certain embodiments are described herein. Variations of those embodiments may become apparent to those of ordinary skill in the art upon reading the foregoing description.

The inventors expect skilled artisans to employ such variations as appropriate, and the inventors intend for the embodiments to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A method of controlling optical feedback in an optical system having a radiation source optically coupled via mode matching optics with a resonant optical cavity having at least two cavity mirrors, one of which is a cavity coupling mirror, the cavity having a plurality of optical resonance cavity modes, wherein the radiation source emits a beam of continuous wave radiation and is capable of being scanned whereby a mean optical frequency of the beam of continuous wave radiation is adjustable over a range of frequencies, wherein the radiation source is responsive to optical feedback radiation emerging from the resonant optical cavity and impinging on the radiation source, and wherein the mode matching optics couples the beam of continuous wave radiation to the resonant optical cavity via the cavity coupling mirror, the method comprising
aligning the radiation source and the mode matching optics to control an amount of the optical feedback radiation emerging from the resonant optical cavity, wherein a mode fill ratio of optical feedback spectral modes is reduced relative to a maximum mode fill ratio, wherein for the maximum mode-fill ratio the beam of continuous wave radiation is coupled with a fundamental cavity spatial mode; and
wherein the aligning the radiation source and the mode matching optics includes:
aligning or setting a relative distance between the radiation source and a component of the mode matching optics to achieve the maximum mode fill ratio, and thereafter
adjusting a shape of the optical feedback spectral modes by adjusting the relative distance between the radiation source and the component of the mode matching optics to attain the reduced mode fill ratio and control the amount of the optical feedback radiation emerging from the resonant optical cavity towards the radiation source.

2. The method of claim 1, wherein the adjusting includes reducing the relative distance between the radiation source and the component of the mode matching optics, so that a beam waist size of the continuous wave radiation beam is diverging at the cavity coupling mirror.

3. The method of claim 1, wherein the adjusting includes increasing the relative distance between the radiation source and the component of the mode matching optics, so that a beam waist of the continuous wave radiation beam is converging at the cavity coupling mirror.

4. The method of claim 1, wherein the adjusting includes moving only the radiation source.

5. The method of claim 1, wherein the adjusting includes moving only the component of the mode matching optics.

6. The method of claim 1, wherein the adjusting includes moving both the radiation source and the component of the mode matching optics.

7. The method of claim 1, wherein the adjusting includes reducing the relative distance between the radiation source and the component of the mode matching optics, so that a beam waist size of the continuous wave radiation beam is smaller or larger than a beam waist size of the radiation circulating in the cavity.

8. The method of claim 1, wherein the cavity has a configuration selected from the group consisting of a ring cavity having three or more cavity mirrors, a linear cavity having two or more cavity mirrors, and a V-shaped cavity having three cavity mirrors.

9. The method of claim 1, wherein the radiation source comprises a laser.

10. The method of claim 1, wherein for the reduced mode-fill ratio the beam of continuous wave radiation is coupled with the fundamental cavity spatial mode.

11. The method of claim 1, further comprising operating the optical system with the relative distance between the radiation source and the component of the mode matching optics set to attain the reduced mode-fill ratio of the optical feedback spectral modes.

12. An optical system, comprising:
a resonant optical cavity having at least two cavity mirrors, one of which is a cavity coupling mirror, the resonant optical cavity having a plurality of optical resonance cavity modes;
a radiation source that emits a beam of continuous wave radiation, wherein the radiation source is capable of being scanned whereby a mean optical frequency of the beam of continuous wave radiation is adjustable over a range of frequencies, and wherein the radiation source is responsive to optical feedback radiation emerging from the resonant optical cavity and impinging on the radiation source;
mode matching optics configured to couple the beam of continuous wave radiation to the resonant optical cavity via the cavity coupling mirror, the mode matching optics including at least one component;
an adjustment mechanism coupled with the at least one component of the mode matching optics and/or the radiation source, the adjustment mechanism configured to adjust a relative position of the radiation source relative to the at least one component of the mode matching optics such that a mode fill ratio of optical feedback spectral modes is reduced relative to a maximum mode fill ratio of the beam, wherein for the maximum mode fill ratio the beam of continuous wave radiation is coupled with a fundamental cavity spatial mode; wherein the adjustment mechanism adjusts the relative position by:
aligning or setting a relative position between the radiation source and the at least one component of the mode matching optics to achieve the maximum mode fill ratio, and thereafter
adjusting a shape of the optical feedback spectral modes by adjusting the relative position between the radiation source and the at least one component of the mode matching optics to attain the reduced mode fill ratio and control an amount of the optical feedback radiation emerging from the resonant optical cavity towards the radiation source, and
a detector configured to measure an intensity of an intra-cavity optical power of radiation circulating in the resonant optical cavity.

13. The optical system of claim 12, wherein the adjustment mechanism includes an actuator configured to adjust the relative position of the radiation source and the at least one component of the mode matching optics in response to a control signal.

14. The optical system of claim 13, wherein the control signal is provided by a control system in response to receiving a user input to adjust the relative position of the radiation source and the at least one component of the mode matching optics.

15. The optical system of claim 13, further comprising a detector configured to measure an intensity of an intra-cavity optical power of radiation circulating in the cavity, wherein the control signal is provided by a control system in response to receiving a feedback signal from the detector.

16. The optical system of claim 13, wherein the cavity has a configuration selected from the group consisting of a ring cavity having three or more cavity mirrors, a linear cavity having two or more cavity mirrors, and a V-shaped cavity having three cavity mirrors.

17. The optical system of claim 13, further including a means for adjusting the mean optical frequency of the radiation source so as to scan the mean optical frequency of the radiation source over a cavity resonance peak.

18. The optical system of claim 13, wherein the cavity is capable of being scanned whereby an optical frequency of a cavity resonance mode peak is adjustable over a range of frequencies.

19. The optical system of claim 18, further including a means for controlling a position of one of the cavity mirrors so as to scan the optical frequency of the cavity resonance mode peak.

20. The optical system of claim 13, further including a detector configured to measure an intensity of the intracavity optical power of radiation circulating in the cavity and to generate a signal representing the intracavity optical power of radiation circulating in the cavity, wherein the cavity includes a gaseous medium including one or more analyte species.

21. The optical system of claim 13, wherein the radiation source comprises a laser.

22. A gas analyzer, comprising:
a resonant optical cavity having at least two cavity mirrors, one of which is a cavity coupling mirror, the resonant optical cavity having a plurality of optical resonance cavity modes, the cavity configured to receive a gaseous medium including one or more analyte species;
a radiation source that emits continuous wave radiation, wherein the radiation source is capable of being scanned whereby a mean optical frequency of the continuous wave radiation is adjustable over a range of frequencies, and wherein the radiation source is responsive to optical feedback radiation emerging from the resonant optical cavity and impinging on the radiation source;
mode matching optics configured to couple the continuous wave radiation to the resonant optical cavity via the cavity coupling mirror, the mode matching optics including at least one component;
an adjustment mechanism coupled with the at least one component of the mode matching optics and/or the radiation source, the adjustment mechanism configured to adjust a relative position of the radiation source relative to the at least one component of the mode matching optics such that a mode fill ratio of optical feedback spectral modes is reduced relative to a maximum mode fill ratio of the continuous wave radiation, wherein for the maximum mode fill ratio the beam of continuous wave radiation is coupled with a fundamental cavity spatial mode; wherein the adjustment mechanism adjusts the relative position by:
aligning or setting a relative position between the radiation source and the at least one component of the mode matching optics to achieve the maximum mode fill ratio, and thereafter
adjusting a shape of the optical feedback spectral modes by adjusting the relative position between the radiation source and the at least one component of the mode matching optics to attain the reduced mode fill ratio and control an amount of the optical feedback radiation emerging from the resonant optical cavity towards the radiation source; and
a detector configured to measure an intensity of the intracavity optical power of radiation circulating in the resonant optical cavity and to generate a signal representing the intracavity optical power of radiation circulating in the resonant optical cavity.

23. The gas analyzer of claim 22, wherein the adjustment mechanism includes an actuator configured to adjust the relative position of the radiation source and the at least one component of the mode matching optics in response to a control signal.

24. The gas analyzer of claim 23, wherein the control signal is provided in response to the control system receiving a feedback signal from the detector.

25. The gas analyzer of claim 23, wherein the control signal is provided in response to the control system receiving a user input to adjust the relative position of the radiation source and the at least one component of the mode matching optics.

26. A method of controlling optical feedback in an optical system having a radiation source optically coupled via mode matching optics with a resonant optical cavity having at least two cavity mirrors, one of which is a cavity coupling mirror, the resonant optical cavity having a plurality of optical resonance cavity modes, wherein the radiation source emits a beam of continuous wave radiation and is capable of being scanned whereby a mean optical frequency of the beam of continuous wave radiation is adjustable over a range of frequencies, wherein the radiation source is responsive to optical feedback radiation emerging from the resonant optical cavity and impinging on the radiation source, and wherein the mode matching optics couples the beam of continuous wave radiation to the resonant optical cavity via the cavity coupling mirror, the method comprising
adjusting a shape of optical feedback spectral modes of the optical feedback radiation fed back to the radiation source from the resonant optical cavity by adjusting a relative distance between the radiation source and a component of the mode matching optics to attain a reduced mode-fill ratio of the optical feedback spectral modes relative to a maximum mode-fill ratio and to control the amount of the optical feedback radiation emerging from the resonant optical cavity towards the radiation source, wherein for the maximum mode-fill ratio the beam of continuous wave radiation is coupled with a fundamental cavity spatial mode.

27. The method of claim 26, wherein for the reduced mode-fill ratio the beam of continuous wave radiation is coupled with the fundamental cavity spatial mode.

28. The method of claim 26, further comprising operating the optical system with the relative distance between the radiation source and the component of the mode matching optics set to attain the reduced mode-fill ratio of the optical feedback spectral modes.

* * * * *